United States Patent
Neumann

(10) Patent No.: US 12,136,352 B2
(45) Date of Patent: Nov. 5, 2024

(54) SYSTEM AND METHOD FOR INITIATING MANUFACTURING OF AN EDIBLE COMBINATION

(71) Applicant: KPN INNOVATIONS, LLC., Lakewood, CO (US)

(72) Inventor: Kenneth Neumann, Lakewood, CO (US)

( * ) Notice: Subject to any disclaimer, the term of this patent is extended or adjusted under 35 U.S.C. 154(b) by 0 days.

(21) Appl. No.: 17/106,557

(22) Filed: Nov. 30, 2020

(65) Prior Publication Data

US 2022/0172644 A1 Jun. 2, 2022

(51) Int. Cl.
| | |
|---|---|
| *G16H 20/60* | (2018.01) |
| *G09B 19/00* | (2006.01) |
| *G16B 40/00* | (2019.01) |
| *G16H 10/20* | (2018.01) |
| *G16H 50/20* | (2018.01) |
| *G16H 50/30* | (2018.01) |
| *G16H 10/60* | (2018.01) |
| *G16H 40/67* | (2018.01) |
| *G16H 50/70* | (2018.01) |

(52) U.S. Cl.
CPC ......... *G09B 19/0092* (2013.01); *G16B 40/00* (2019.02); *G16H 10/20* (2018.01); *G16H 20/60* (2018.01); *G16H 50/30* (2018.01); *G16H 10/60* (2018.01); *G16H 40/67* (2018.01); *G16H 50/20* (2018.01); *G16H 50/70* (2018.01)

(58) Field of Classification Search
None
See application file for complete search history.

(56) References Cited

U.S. PATENT DOCUMENTS

| | | | |
|---|---|---|---|
| 10,319,477 B1 * | 6/2019 | Bill | G01N 33/92 |
| 10,768,169 B2 | 9/2020 | Rezzi et al. | |
| 2002/0004749 A1 * | 1/2002 | Froseth | G06Q 10/101 |
| | | | 705/16 |
| 2006/0081653 A1 * | 4/2006 | Boland | G16H 50/30 |
| | | | 222/243 |

(Continued)

OTHER PUBLICATIONS

Derossi et al, Manufacturing Personalized Food for People Uniqueness. An Overview From Traditional to Emerging Technologies, Jan. 2019, Critical Reviews in Food Science and Nutrition, 60:7, 1141-1159 (Year: 2019).*

(Continued)

*Primary Examiner* — Gregory Lultschik
(74) *Attorney, Agent, or Firm* — Caldwell Intellectual Property Law

(57) ABSTRACT

A system and method for initiating manufacturing of an edible combination includes a computing device, the computing device configured to identify at least a biochemical profile as a function of a first biological extraction, generate at least a new profile as a function of a second biological extraction, produce at least a self-based nutritional program, wherein producing further comprises determining at least a corporeal variation as a function of the biochemical profile and the new profile using at least an analysis process, identifying a nutritional deficiency as a function of the corporeal variation, and producing the self-based nutritional program as a function of the nutritional deficiency, and initiate at least manufacturing of an edible combination as a function of the at least self-based nutritional program.

12 Claims, 7 Drawing Sheets

(56) References Cited

U.S. PATENT DOCUMENTS

| | | | | |
|---|---|---|---|---|
| 2008/0221932 | A1* | 9/2008 | Kane | G16H 10/20 705/3 |
| 2009/0307007 | A1* | 12/2009 | Hermann | G16H 20/40 705/2 |
| 2010/0266723 | A1* | 10/2010 | Bralley, III | G16H 20/60 426/2 |
| 2012/0130732 | A1* | 5/2012 | Blander | G16H 10/20 705/2 |
| 2013/0216982 | A1* | 8/2013 | Bennett | A61B 5/7275 434/127 |
| 2014/0113885 | A1* | 4/2014 | Thadhani | C12Q 1/6883 514/167 |
| 2015/0269865 | A1* | 9/2015 | Volach | G09B 19/0092 434/127 |
| 2016/0106142 | A1* | 4/2016 | Contractor | A23P 20/20 99/516 |
| 2017/0139385 | A1* | 5/2017 | Young | G09B 19/0092 |
| 2017/0148348 | A1* | 5/2017 | Hardee | G01N 33/20 |
| 2017/0370910 | A1* | 12/2017 | Rezzi | G01N 33/5308 |
| 2019/0145988 | A1* | 5/2019 | Haddad | G16H 20/60 514/52 |
| 2019/0152663 | A1* | 5/2019 | Kraft | A61J 3/074 |
| 2019/0251861 | A1* | 8/2019 | Wolf | G16H 20/60 |
| 2020/0133235 | A1* | 4/2020 | El-Tahry | G05B 19/4099 |
| 2020/0146994 | A1* | 5/2020 | Albed Alhnan | B29C 64/336 |

OTHER PUBLICATIONS

Sun et al, A Review on 3D Printing for Customized Food Fabrication, 2015, 43rd Proceedings of the North American Manufacturing Research Institute of SME, vol. 1, 308-319 (Year: 2015).*

Wegrzyn et al, Food Layered Manufacture: A New Process for Constructing Solid Foods, 2012, Trends in Food Science & Technology, vol. 27, 66-72 (Year: 2012).*

Lipton et al, Additive Manufacturing for the Food Industry, 2015, Trends in Food Science & Technology, vol. 43, 114-123 (Year: 2015).*

Rankin, What's New in 3D Printing, Part IV: OctoPrint, 2016, Linux Journal (Year: 2016).*

Pataranutaporn et al, Wearable Lab on Body: Combining Sensing of Biochemical and Digital Markers in a Wearable Device, 2019, 2019 41st Annual International Conference of the IEEE Engineering in Medicine and Biology Society (EMBC), pp. 3330-3332 (Year: 2019).*

McCaul et al, Challenges and opportunities in wearable technology for biochemical analysis in sweat, 2017, Current Opinion in Electrochemistry, vol. 3, Issue 1, pp. 46-50 (Year: 2017).*

Pico et al, Biomarkers of Nutrition and Health: New Tools for New Approaches, May 2019, 11, p. 1092 (Year: 2019).*

* cited by examiner

SYSTEM AND METHOD FOR INITIATING MANUFACTURING OF AN EDIBLE COMBINATION

FIELD OF THE INVENTION

The present invention generally relates to the field of manufacturing. In particular, the present invention is directed to a system and method for initiating manufacturing of an edible combination.

BACKGROUND

A number of parameters or compounds define the nutritional status of a subject making an edible recommendation challenging. This is further complicated by the overwhelming amount of biological studies that identify a plurality of compounds relating to a singular metabolic state. The lack of metabolic monitoring prevents reasonable edibles from being recommended.

SUMMARY OF THE DISCLOSURE

In an aspect a system for initiating manufacturing of an edible combination includes a computing device, the computing device configured to identify at least a biochemical profile as a function of a first biological extraction, generate at least a new profile as a function of a second biological extraction, produce at least a self-based nutritional program, wherein producing further comprises determining at least a corporeal variation as a function of the biochemical profile and the new profile using at least an analysis process, identifying a nutritional deficiency as a function of the corporeal variation, and producing the self-based nutritional program as a function of the nutritional deficiency, and initiate at least manufacturing of an edible combination as a function of the at least self-based nutritional program.

In another aspect a method for initiating manufacturing of an edible combination includes identifying, by a computing device, at least a biochemical profile as a function of a first biological extraction, generating, by the computing device, at least a new profile as a function of a second biological extraction, producing, by the computing device, at least a self-based nutritional program, wherein producing further comprises determining at least a corporeal variation as a function of the biochemical profile and the new profile using at least an analysis process, identifying a nutritional deficiency as a function of the corporeal variation, and producing the self-based nutritional program as a function of the nutritional deficiency, and initiating, by the computing device, at least manufacturing of an edible combination as a function of the at least self-based nutritional program.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for initiating manufacturing of an edible combination. In an embodiment, initiating manufacturing of an edible combination includes identifying at least a biochemical profile. Aspects of the present disclosure can be used to generate a new profile and produce a self-based nutritional program. This is so, at least in part, because an analysis process is used on the biochemical profile and new profile. Aspects of the present disclosure allow for initiating the manufacturing of an edible combination. Exemplary embodiments illustrating aspects of the present disclosure are described below in the context of several specific examples.

Figure 1:
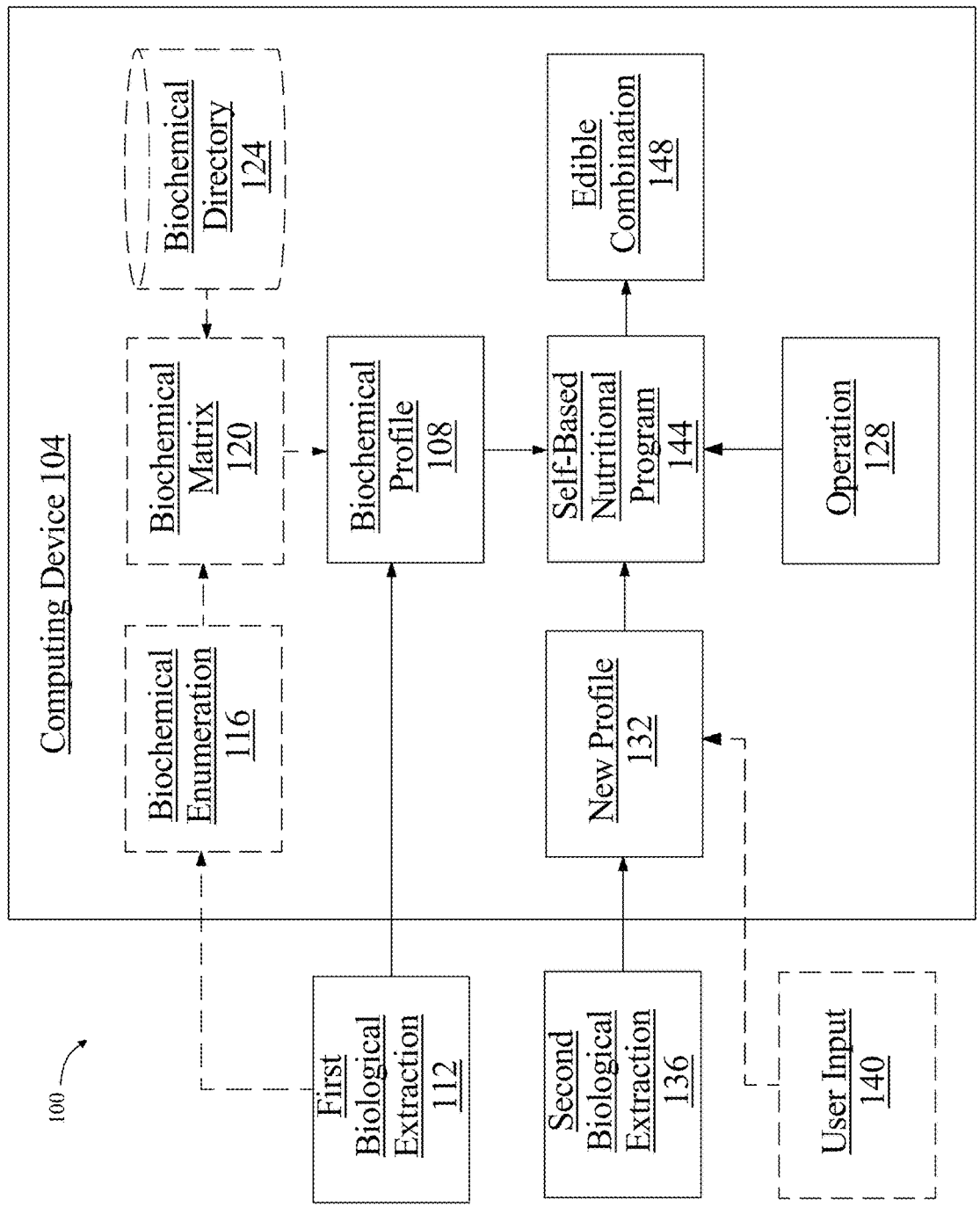
FIG. 1 is a block diagram illustrating an exemplary embodiment of a system for initiating manufacturing of an edible combination.

Referring now to FIG. 1, an exemplary embodiment of a system 100 for initiating manufacturing of an edible combination is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to identify at least a biochemical profile 108. As used in this disclosure "biochemical profile" is an profile that relates to at least a biochemical status of an individual, wherein a biochemical status is an element of data that pertains to a user's health. For example, and without limitation, biochemical profile 108 may indicate that a user has elevated LDL present in the circulatory system. As a further non-limiting example biochemical profile 108 may indicate that a user has a risk of developing diabetes. Biochemical profile 108 is identified as a function of a first biological extraction 112. As used in this disclosure "first biological extraction" is at least an element of user biological data. As used in this disclosure, "biological data" is data indicative of a person's biological state; biological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. First biological extraction 112 may include at least a marker associated with a biochemical status of an individual. As used in this disclosure a "marker" is a biochemical datum that may pertain to a biochemical status of an individual. For instance, and without limitation, the marker may include a particular set of biomarkers, test results, and/or biochemical information that is recognized in a given medical field as useful for identifying biochemical statuses of individuals within a relevant field. As a non-limiting example, and without limitation, marker describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. Biological extraction data may alternatively or additionally include any data used as a biological extraction as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," the entirety of which is incorporated herein by reference. Additionally or alternatively, biochemical profile 108 may be determined according to any processes used as a determination process as described in U.S. Nonprovisional application Ser. No. 16/502,835.

Still referring to FIG. 1, first biological extraction 112 may be identified as a function of one or more monitoring devices. As used in this disclosure "monitoring device" is an electronic device that is worn on the person of a user, such as without limitation close to and/or on the surface of the skin, wherein the device can detect, analyze, and transmit biochemical information concerning an individual. The monitoring device may include, without limitation, any device that further collects, stores, and analyzes data associated with biochemical profile 108. The monitoring device my consist of, without limitation, near-body electronics, on-body electronics, in-body electronics, electronic textiles, smart watches, smart glasses, smart clothing, fitness trackers, body sensors, wearable cameras, head-mounted displays, body worn cameras, Bluetooth headsets, wristbands, smart garments, chest straps, sports watches, fitness monitors, and the like thereof. The monitoring device may include directed light monitoring devices such as spectrophotometric device at least identify concentrations of markers and/or identify one or more user biochemical statuses such as body mass index, fat percentage, water percentage, bone mass percentage, muscle mass percentage, and the like thereof. The monitoring device may include, without limitation, earphones, earbuds, headsets, bras, suits, jackets, trousers, shirts, pants, socks, bracelets, necklaces, brooches, rings, jewelry, AR HMDs, VR HMDs, exoskeletons, location trackers, and gesture control wearables. The monitoring device may include one or more medical devices that are operated by one or more informed advisors, wherein an informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like. As a non-limiting example, a medical device of a/an stethoscope, ultrasound device, MRI device, PET scanner, CT scanner, X-ray device, electrocardiogram device, and the like thereof.

Still referring to FIG. 1, the monitoring device may identify one or more biochemical concentrations. As used in this disclosure "biochemical concentration" is the relative amount of a given marker contained within a specific volume and or mass of an individual. As a non-limiting example, a biochemical concentration may be identified as 5 ng/mL of a first marker in an individual's circulatory system. As a further non-limiting example a biochemical concentration may identify a value of 500 ppb of isoprene in the breath of an individual.

Still referring to FIG. 1, computing device 104 may produce at least a biochemical enumeration 116 as a function of first biological extraction 112. As used in this disclosure a "biochemical enumeration" is an enumeration of one or more quantitative values that at least relates to the first biological extraction. As a non-limiting example first biological extraction 112 may denote a biochemical concentration of 10 mg/L for albumin blood serum, wherein a biological enumeration of 27 may be produced. As a further non-limiting example a biochemical concentration of 5 ng/mL for c reactive protein, wherein a biological enumeration of 93 may be produced. Biochemical enumeration 116 may include one or more vectors that at least relate to the first biological extraction. As used in this disclosure a "vector" as defined in this disclosure is a data structure that represents one or more a quantitative values and/or measures relating to the first biological extraction. A vector may be represented as an n-tuple of values, where n one or more values, and may include two or more values or any other quantity, as described in further detail below; a vector may alternatively or additionally be represented as an element of a vector space, defined as a set of mathematical objects that can be added together under an analysis process of addition following properties of associativity, commutativity, existence of an identity element, and existence of an inverse element for each vector, and can be multiplied by scalar values under an analysis process of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute 1 as derived using a Pythagorean norm: $l=\sqrt{\Sigma_{i=0}^{n} a_i^2}$, where ai is attribute number i of the vector. Scaling and/or normalization may function to make vector comparison independent of absolute quantities of attributes, while preserving any dependency on similarity of attributes.

Still referring to FIG. 1, computing device 104 may produce biochemical enumeration 116 as a function of an effect concentration. As used in this disclosure "effect concentration" is a set concentration that elucidates one or more impacts on the user, wherein an impact is a physiologic response and/or action. For example, and without limitation an effect concentration may identify a set value of 80% for 02 saturation, wherein below 80% an effect of lethargy may be experienced by an individual. As a further non-limiting example an effect concentration of 100 ng/mL of glucose in the circulatory system may be identified such that an effect may be incapacitation due to hypoglycemia if the individual's glucose concentration falls below that value.

Still referring to FIG. 1, computing device 104 may generate a biochemical matrix 120 as a function of biological enumeration 116 and a biochemical directory 124, wherein a biochemical directory, is a database relating to one or more markers associated with the user biochemical status, as described below. As used in this disclosure "biochemical matrix" is an array and/or table of numbers, expressions, symbols, and/or representations arranged in rows and/or columns. Biochemical matrix 120 may be arranged such that each number, expression, symbol, and/or representation relates to a specific marker associated with a user biochemical status. Biochemical matrix 120 may be comprised of one or more vectors, wherein a vector is described above. As a non-limiting example, biochemical matrix 120 may arrange 6 markers in a 3 row and 2 column array, wherein each marker has its own row and column combination that at least identifies that marker and the number, expression, symbol, and/or representation associated with the marker. As a non-limiting example, biochemical directory 124 may identify the marker IL-13 as a disease marker for a urinary disease. As a further non-limiting example biochemical directory 124 may identify the marker serotonin for a good user biochemical status. Biochemical matrix 120 may be generated as a function of one or more machine-learning processes. A "machine-learning process," as used in this disclosure, is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language The machine-learning processes may enhance, tune, and/or otherwise derive numbers, expressions, symbols, representations, and/or vectors that exist within biochemical matrix 120. As a non-limiting example the machine-learning process may establish, enhance, and/or modify coefficients in a system of equations for generating and/or modifying biochemical matrix 120. Biochemical matrix 120 may alternatively or additionally include any machine-learning process used as a machine-learning process as described in U.S. Nonprovisional application Ser. No. 16/837,113, filed on Apr. 1, 2020, and entitled "SYSTEMS AND METHODS FOR GENERATING ALIMENTARY INSTRUCTION SETS BASED ON VIBRANT CONSTITUTIONAL GUIDANCE," the entirety of which is incorporated herein by reference.

Still referring to FIG. 1, computing device 104 may determine biochemical directory 124 as a function of at least a first biochemical matrix of an individual and at least a second biochemical matrix using an analysis process 128. As used in this disclosure an "analysis process" is a matrix operation which takes zero or more input values from one or more matrices and produces a well-defined output matrix and/or enumeration. Analysis process 128 may include, without limitation, basic operations such as addition, scalar multiplication, transposition, matrix multiplication, row operations, submatrix operations, and the like there of. Additionally or alternatively, analysis process 128 may include without limitation linear equations, linear transformations, trace operations, determinant operations, eigenvalues and/or eigenvectors. As a non-limiting example an analysis process may include finitary analysis processes. As used in this disclosure "finitary analysis processes" are algorithms containing a finite number of input values. Finitary analysis processes may be translated into a finite set of symbolic prepositions starting from a finite set of axioms. As a non-limiting example a finitary analysis process may include addition, subtraction, multiplication, division, averages, standard deviations, and the like thereof. Additionally or alternatively, analysis process 128 may include partial analysis processes. As used in this disclosure "partial analysis processes" are algorithms having a binary relation over two sets, wherein every element of the first set relates to at most one element of the second set. Partial analysis processes generalize the concept of a function by not requiring every element of the first set to be associated to exactly one element of the second set. For example, and without limitation a first biochemical enumeration may be associated with more than one second biochemical enumerations. As used in this disclosure "second biochemical matrix" is at least a second array and/or table of numbers, expressions, symbols, and/or representations arranged in rows and/or columns that relate to an individual. As a non-limiting example biochemical directory 124 may be determined as a function of averaging the first biochemical matrix and the second biochemical matrix to determine an average biochemical matrix, which may be used to determine biochemical directory 124.

Still referring to FIG. 1, computing device 104 is configured to generate at least a new profile 132 as a function of a second biological extraction 136. As used in this disclosure "new profile" is an element that relates to an updated and/or modified biochemical status of an individual, wherein an updated and/or modified biochemical status is an element that at least differs from the first health state of the individual. As a non-limiting example a new profile may be generated that at least determines a change and/or alteration in at least a marker. As used in this disclosure "second biological extraction" is at least a second element of user biological data that at least relates to new profile 132. Second biological extraction 136 may be generated as a function of the monitoring device, wherein the monitoring device is discussed in detail above. Second biological extraction 136 may or may not relate to first biological extraction 112. As a non-limiting example a first biological extraction may relate to markers associated with the circulatory system of an individual, wherein a second biological system may relate to markers associated with the lymphatic system. As a further non-limiting example a first biological extraction may relate to markers associated with the muscular system of an individual, wherein the second biological extraction may also relate to markers associated with the muscular system of the individual.

Still referring to FIG. 1, computing device 104 may generate new profile 132 by receiving at least a user input 140. As used in this disclosure "user input" is a soft requirement provided by the users, in addition to the user profile, that reflects a wish, desire, want, and/or urge regarding a user biochemical status. User input 140 may be obtained from one or more graphical user interfaces. As used in this disclosure "graphical user interface" is a form or other graphical element having data entry fields, where a user may select one or more fields to enter one or more elements relating to new profile 132. User input 140 may relate to at least a desired nutritional program that the user prefers, wherein a nutritional program may include intermittent fasting, plant-based diets, low-carb diets, paleo diets, low-fat diets, Mediterranean diets, keto diets, and the like thereof. User input 140 may relate to previous medical records that at least relate to a user biochemical status. User input 140 may relate to a user physical activity level, wherein a physical activity level is a categorized level that relates to the magnitude of strenuous activity the user may or may not exhibit.

Still referring to FIG. 1, computing device 104 is configured to produce at least a self-based nutritional program 144. As used in this disclosure "self-based nutritional program" is an program that identifies edibles that at least enhance a user's biochemical status. Self-based nutritional program 144 is generated as a function of a corporeal variation. As used in this disclosure "corporeal variation" is a user status that relates the previous biochemical profile to the new profile. Computing device 104 may determine at least a corporeal variation as a function of biochemical profile 108 and new profile 132 using analysis process 128. As a non-limiting example the corporeal variation may be generated using analysis process 128 such that a subtraction among new profile 132 and biochemical profile 108 results in a difference of individual markers, numbers, signs, expressions, and/or representations. As a non-limiting example the corporeal variation may be generated using analysis process 128 such that an addition among new profile 132 and biochemical profile 108 results in modified individual markers, numbers, signs, expressions, and/or representations, wherein the modified individual markers, numbers, signs, expressions and/or representations are then divided by the number of profiles to produce an average of the profiles. The corporeal variation may be generated as a function of finitary analysis processes, wherein finitary analysis processes have a finite number of input values as described above in detail. The corporeal variation may be generated as a function of partial analysis processes, wherein a partial analysis process is a binary relation over two sets that associates to every element of the first set at most one element of the second set, as described above in detail. Computing device 104 identifies a nutritional deficiency as a function of the corporeal variation. As used in this disclosure a "nutritional deficiency" is a deficiency of a nutrient that exists in the user's body, wherein a nutrient is described in detail below. As a non-limiting example, a nutritional deficiency may include a marker that is 1 ng/mL, wherein the marker should be 100 ng/mL in the user's body. Computing device 104 produces self-based nutritional program 144 as a function of the identified nutritional deficiency. Self-based nutritional program 144 may alternatively or additionally include any nutritional program as described in U.S. Nonprovisional application Ser. No. 16/837,113.

Still referring to FIG. 1, computing device 104 may produce self-based nutritional program 144 as a function of a threshold matrix. As used in this disclosure a "threshold matrix" is an array and/or table of numbers, expressions, symbols, and/or representations arranged in rows and/or columns that establishes at least a minimum for each number, expression, symbol, and/or representation. Threshold matrix may consist of one or more corporeal variations that at least generate threshold matrix. As a non-limiting example a threshold matrix may contain 8 corporeal variations that are arranged among 4 rows and 2 columns, wherein each value in the array specifies a corporeal variation that may consist of a value that a marker may not fall below, such as a value of 4 for row 3, column 2. As a further non-limiting example a threshold matrix may contain 24 corporeal variations that are arranged in 4 rows and 6 columns, wherein each corporeal variation in the array specifies a value that a marker may not exceed, such as a value of 12 for row 2, column 2. The threshold matrix may be generated as a function of analysis process 128, wherein the analysis process may consist of a finitary analysis process, a partial analysis process, and/or a traditional analysis process, wherein a traditional analysis process is unary analysis processes such as negation and trigonometric functions. The threshold matrix may be generated as a function of analysis process 128 using new profile 132 and at least a nutritional threshold. As used in this disclosure a "nutritional threshold" is a value that at least relates to a minimum and/or maximum value that a nutrient should be in the user's body. As used in this disclosure "nutrient" is a substance that provides nourishment essential for growth and maintenance of life. For instance, and without limitation, a nutrient may consist of an amino acid. As a further non-limiting example a nutrient may consist of a vitamin. The nutritional threshold may be a value of 6 for the nutrient sodium chloride, wherein the nutritional threshold may be a value of 12 for vitamin C. The machine learning process may alternatively or additionally include any machine-learning process as described in U.S. Nonprovisional application Ser. No. 16/837,113.

Still referring to FIG. 1, the nutritional threshold may be identified as a function of biochemical profile 108 and at least a nutritional directory, wherein a nutritional directory is described in detail below. As a non-limiting example a nutritional directory may relate to specific nutrients that an individual must possess in specific concentrations, such that the individual may remain healthy. Biochemical profile 108 may be utilized to establish a baseline and/or reference point for a user biochemical status, such that the nutritional threshold may be identified as a function of the baseline values. Additionally or alternatively, the baseline and/or reference point may be compared to the nutritional directory such that the baseline and/or reference point may be altered and/or modified to at least generate the nutritional threshold.

Still referring to FIG. 1, computing device 104 is configured to initiate at least manufacturing of an edible combination 148 as a function of self-based nutritional program 144. As used in this disclosure "edible combination" is at least one or more edibles that at least fulfill nutritional self-based nutritional program 144. Edible combination 148 may include one or more foods that at least provide energy, nutrients and/or allow for growth. Edible combinations may include meats, plants, fungi, and the like thereof. Computing device 104 may initiate manufacturing of edible combination 148 using an automated manufacturing system, wherein an automated manufacturing system includes an additive manufacturing device and a controller that controls one or more manufacturing steps automatically, as described further below. Computing device may alternatively or additionally include any automated manufacturing system used as an automated manufacturing system as described in U.S. Nonprovisional application. Ser. No. 16,911,994, filed on Jun. 25, 2020, and entitled "METHODS AND SYSTEMS FOR ADDITIVE MANUFACTURING OF NUTRITIONAL SUPPLEMENT SERVINGS," the entirety of which is incorporated herein by reference. Computing device 104 may initiate manufacturing of edible combination 148 by transmitting a signal to a provisioner. As used in this disclosure a "signal" is a notification and/or indicator that an edible combination should be manufactured. A signal may consist of a wired and/or wireless communication. The wireless communication signals may include, without limitation, radio waves, electric fields, mobile broadband, Wi-Fi, and/or the BLUETOOTH protocol promulgated by Bluetooth SIG, Inc. of Kirkland, Washington, wherein Bluetooth is a wireless technology used for exchanging data between fixed mobile devices over short distances using ultra high frequency radio waves between 2.402 GHz to 2.480 GHz. As a non-limiting example computing device 104 may initiate manufacturing via Bluetooth, with a provisioner, that at least notifies provisioner to manufacture edible combination 148. As used in this disclosure a "provisioner" is an entity and/or person that produces edibles of a plurality of edibles. Provide examples of an edible combination. As a non-limiting example a provisioner may include a grocery store, restaurant, edible-delivery service, manufacturing facility, and the like thereof.

Still referring to FIG. 1, computing device 104 may initiate the manufacturing of edible combination 148 by determining at least an edible index using at least an edible directory, wherein an edible directory is a database that stores a list of types of edibles, as described in detail below. As used in this disclosure an "edible index" is at least a value associated with each edible and/or edible combination. As a non-limiting example an edible index may be 10 for an edible of an apple. The edible index may be 2, 3, and 5, for an edible of a banana, wherein each value is associated with a respective nutrient such as vitamins, amino acids, and carbohydrates.

Figure 2:
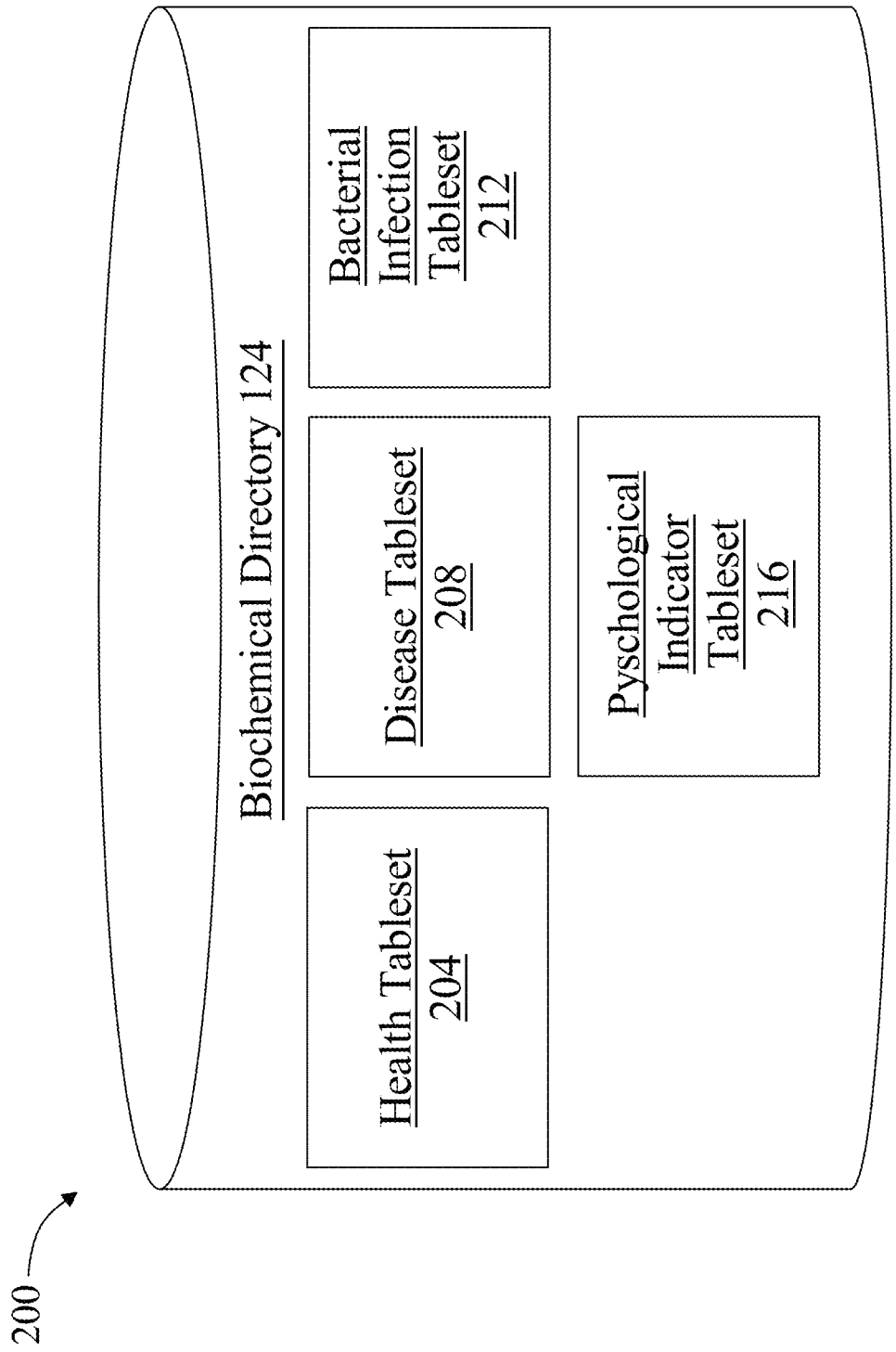
FIG. 2 is a block diagram of an exemplary embodiment of a biochemical directory according to an embodiment of the invention.

Now referring to FIG. 2, an exemplary embodiment 200 of biochemical directory 124 according to an embodiment of the invention is illustrated. As used in this disclosure "biochemical directory" is a database that relates to one or more markers associated with the user biochemical status. Biochemical directory 124 may be implemented, without limitation, as a relational databank, a key-value retrieval databank such as a NOSQL databank, or any other format or structure for use as a databank that a person skilled in the art would recognize as suitable upon review of the entirety of this disclosure. Biochemical directory 124 may alternatively or additionally be implemented using a distributed data storage protocol and/or data structure, such as a distributed hash table or the like. Biochemical directory 124 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Biochemical directory 124 may include a health tableset 204. Health tableset 204 may indicate markers associated with a healthy user status. As a non-limiting example, health tableset 204 may include albumin, IL-3, omega-3 fatty acid, isoprene, systolic blood pressure, diastolic blood pressure, pulse pressure, resting pulse rate, total homocysteine, total cholesterol, low-density lipoprotein (LDL), very low density lipoprotein (VLDL), high-density lipoprotein (HDL), triglycerides, fasting glucose, glycosylated hemoglobin (HbA1c), body mass index (BMI), waist to hip ratio, leptin, adiponectin, c-reactive protein, norepinephrine, epinephrine, creatinine, cystatin C, peak expiratory flow, EKG, and the like thereof. Biochemical directory 124 may include a disease tableset 208. Disease tableset 208 may indicate markers associated with a disease user status. As a non-limiting example, disease tableset 208 may include sCRP, LPLAC2, MPO, Lp(a), lipid particle fractionation, microbiome, cardiac flow imaging, troponin levels, exercise stress test, echocardiogram, cTn, hs-cTn, H-FABP, GDF-15, fibrinogen, UA, Papp-A, MMPs, Lp-PLA2, sPLA2, sCD40L, copeptin, MR-proADM, NPs, ST2, ET-1, Gal-3, NRG-1, MicroRNAs, and the like thereof. Biochemical directory 124 may include a bacterial infection tableset 212. Bacterial infection tableset 212 may indicate markers associated with a bacterial infection user status. As a non-limiting example, bacterial infection tableset 212 may include BB_A68, BB_A64, BB_A74, BB_K32, V1sE_C6, BB_A15, BB_B19, BB_032, BB_A24, BB_0147, CRP, IL-6, PCT, Serum Amyloig A (SAA), ESR, sTREM-1, ANP, PSP, IL-8, IL-27, suPAR, and the like thereof. Biochemical directory 124 may include a psychological indicator tableset 216. Psychological indicator tableset 216 may indicate markers associated with a psychological disorder user status. As a non-limiting example, psychological indicator tableset 216 may include CRP, IL-6, TNF alpha, brain-derived neurotrophic factor (BDNF), apolipotein C3, epidermal growth factor, cortisol, resistin, prolactin, myeloperoxidase, cytokines, insulin-derived growth factors, malondialdehyde (MDA), urinary isoprostranes, miRNA, ammonia, ethylene, EEG, norepinephrine, monoamine oxidase, 3-methoxy-4-hydroxyphenylethylene glycol, cortisol, zinc, MRI, spermidine, N1-acetyltransferase 1, and the like thereof.

Figure 3:
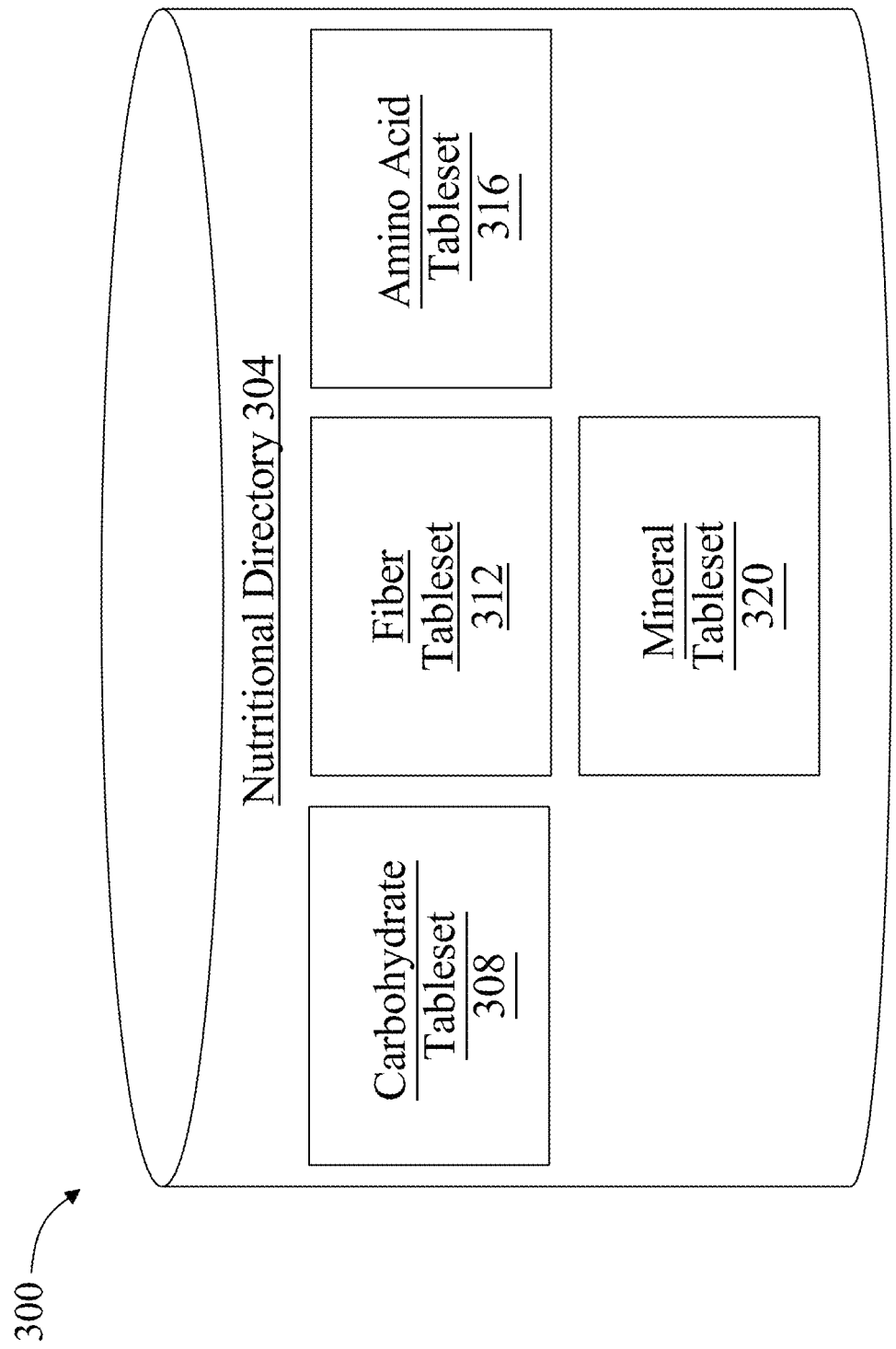
FIG. 3 is a block diagram of an exemplary embodiment of a nutritional directory according to an embodiment of the invention.

Now referring to FIG. 3, an exemplary embodiment 300 of a nutritional directory 304 according to an embodiment of the invention is illustrated. Nutritional directory 304 may be implemented, without limitation, as a relational databank, a key-value retrieval databank such as a NOSQL databank, or any other format or structure for use as a databank that a person skilled in the art would recognize as suitable upon review of the entirety of this disclosure. Nutritional directory 304 may alternatively or additionally be implemented using a distributed data storage protocol and/or data structure, such as a distributed hash table or the like. Nutritional directory 304 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Nutritional directory 304 may include a carbohydrates tableset 308. Carbohydrates tableset 308 may relate to types of carbohydrates that at least provide necessary nutritional values. As a non-limiting example, carbohydrate tableset 308 may include monosaccharides, disaccharides, oligosaccharides, polysaccharides, and the like thereof. Nutritional directory 304 may include a fiber tableset 312. Fiber tableset 312 may relate to types of fiber that at least provide necessary nutritional values. As a non-limiting example, fiber tableset 312 may include soluble fiber, such as beta-glucans, raw guar gum, psyllium, inulin, and the like thereof as well as insoluble fiber, such as wheat bran, cellulose, lignin, and the like thereof. Nutritional directory 304 may include an amino acids tableset 316. Amino acids tableset 316 may relate to types of amino acids that at least provide necessary nutritional values. As a non-limiting example, amino acids tableset 316 may include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Nutritional directory 304 may include a minerals tableset 320. Minerals tableset 320 may relate to types of minerals that at least provide necessary nutritional values. As a non-limiting example, minerals tableset 320 may include calcium, phosphorous, magnesium, sodium, potassium, chloride, sulfur, iron, manganese, copper, iodine, zing, cobalt, fluoride, selenium, and the like thereof.

Figure 4:
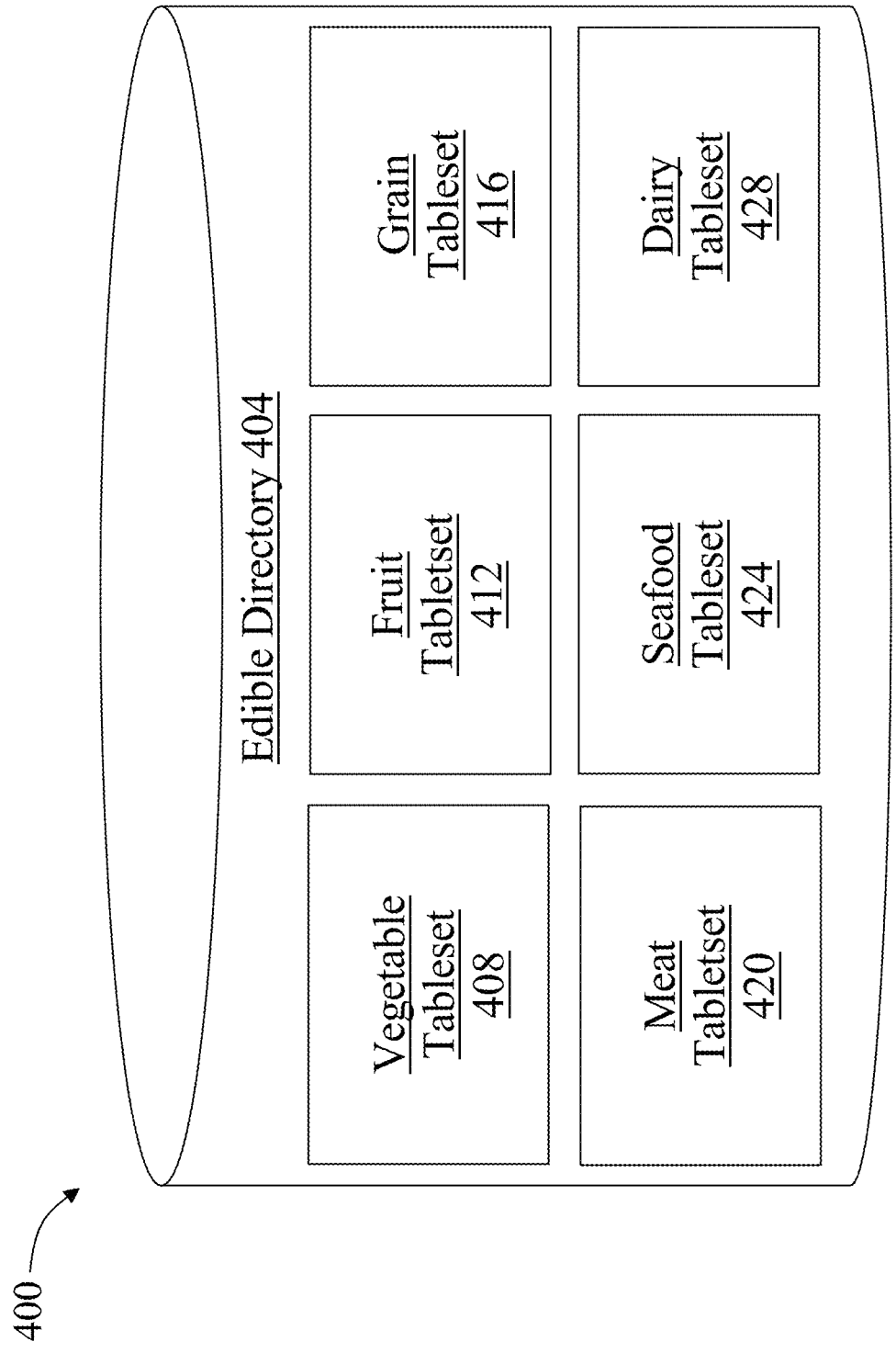
FIG. 4 is a block diagram of an exemplary embodiment of an edible directory according to an embodiment of the invention.

Now referring to FIG. 4, an exemplary embodiment 400 of an edible directory 404 according to an embodiment of the invention is illustrated. Edible directory 404 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 404 may alternatively or additionally be implemented using a distributed data storage protocol and/or data structure, such as a distributed hash table or the like. Edible directory 404 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 404 may include a vegetable tableset 408. Vegetable tableset 408 may relate to types of edibles that may be vegetables. As a non-limiting example, vegetable tableset 408 may include leafy and salad vegetables, edible flowers, podded vegetables, bulb and stem vegetables, root and tuberous vegetables, sea vegetables, and the like thereof. Edible directory 404 may include a fruit tableset 412. Fruit tableset 412 may relate to types of edibles that may be fruits. As a non-limiting example, fruit tableset 412 may include simple fruit, aggregate fruit, multiple fruit, berries, accessory fruit, seedless fruit, true berry fruit, pepo fruit, hesperidium fruit, and the like thereof. Edible directory 404 may include a grain tableset 416. Grain tableset 416 may relate to types of edibles that may be grains. As a non-limiting example, grain tableset 416 may include teff, wheat, oats, rice, corn, barley, sorghum, rye, millet, triticale, amaranth, buckwheat, quinoa, and the like thereof. Edible directory 404 may include a meat tableset 420. Meat tableset 420 may relate to types of edibles that may be meats. As a non-limiting example, meat tableset 420 may include chicken, sheep, rabbit, pig, cattle, bison, ostrich, deer, goat, horse, dog, cat, guinea pig, whale, zebra, antelope, camel, crocodile, water buffalo, and the like thereof. Edible directory 404 may include a seafood tableset 424. Seafood tableset 424 may relate to types of edibles that may be seafood. As a non-limiting example, seafood tableset 424 may include fish, roe, crustaceans, Mollusca, echinoderms, medusozoan, tunicates, and the like thereof. Edible directory 404 may include a dairy tableset 428. Dairy tableset 428 may relate to types of edibles that may be dairy. As a non-limiting example, dairy tableset 428 may include milk, fermented milk, yogurt, cream, butter, cheese, casein, custard, ice cream, and the like thereof.

Figure 5:
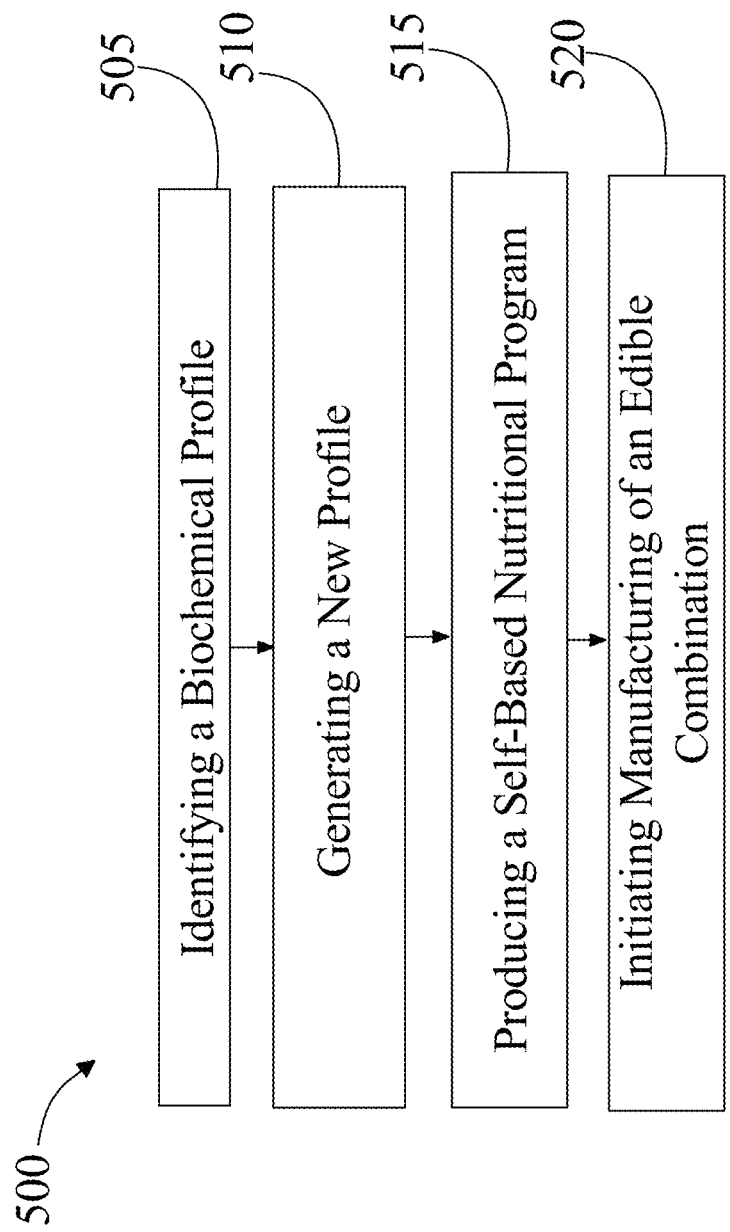
FIG. 5 is a process flow diagram illustrating an exemplary embodiment of a method for initiating manufacturing of an edible combination.

Now referring to FIG. 5, an exemplary embodiment of a method 500 for initiating manufacturing of an edible combination is illustrated. At step 505, a computing device 104 identifies a biochemical profile 108 as a function of a first biological extraction 112. Biochemical profile 108 includes any of the biochemical profile 108 as described above, in reference to FIGS. 1-4. First biological extraction 112 includes any of the first biological extraction 112 as described above, in reference to FIGS. 1-4. Biochemical profile may be generated as a function of a biochemical matrix 120. Biochemical matrix 120 includes any of the biochemical matrix 120 as described above, in reference to FIGS. 1-4. Biochemical matrix 120 may be generated as a function of a biochemical enumeration 116 and a biochemical directory 124. Biochemical enumeration 116 includes any of the biochemical enumeration 116 as described above, in reference to FIGS. 1-4. Biochemical directory 124 includes any of the biochemical directory 124 as described above, in reference to FIGS. 1-4. Biochemical profile 108 may be identified as a function of an analysis process 128. Analysis process 128 includes any of the analysis process 128 as described above, in reference to FIGS. 1-4. As a non-limiting example computing device 104 may identify a biochemical profile of a healthy individual as a function of a first biological extraction of a heart rate monitor.

With continued reference to FIG. 5, at step 510, computing device 104 generates at least a new profile 132 as a function of a second biological extraction 136. New profile 132 includes any of the new profile 132 as described above, in reference to FIGS. 1-4. Second biological extraction 136 includes any of the second biological extraction 136 As described above, in reference to FIGS. 1-4. New profile 132 may be generated as a function of a user input 140. User input 140 includes any of the user input 140 as described above, in reference to FIGS. 1-4. For instance, and without limitation, new profile !!8 may be identified as a function of a second biological extraction of a blood pressure elevation and a user input of hypercholesterolemia.

With continued reference to FIG. 5, at step 515, computing device 104 produces at least a self-based nutritional program 144 as a function of the at least biochemical profile 108 and at least new profile 132 using at least analysis process 128. Self-based nutritional program 144 includes any of the self-based nutritional program 144 as described above, in reference to FIGS. 1-4. For instance, and without limitation, self-based nutritional program 144 may be produced as a function of a biochemical profile that identifies a baseline level of nutrients, wherein the new profile identifies a lower level of a nutrient than the baseline, wherein the self-based nutritional program may determine an edible to at least correct that nutrient.

Still referring to FIG. 5, at step 520, computing device 104 initiates at least manufacturing of an edible combination 148 as a function of self-based nutritional program 144. Edible combination 148 includes any of the edible combination 148 as described above, in reference to FIGS. 1-4. For instance, and without limitation, computing device 104 may initiate manufacturing of edible combination 148 by transmitting a notification to a provisioner, that at least is capable of producing the edible combination.

Figure 6:
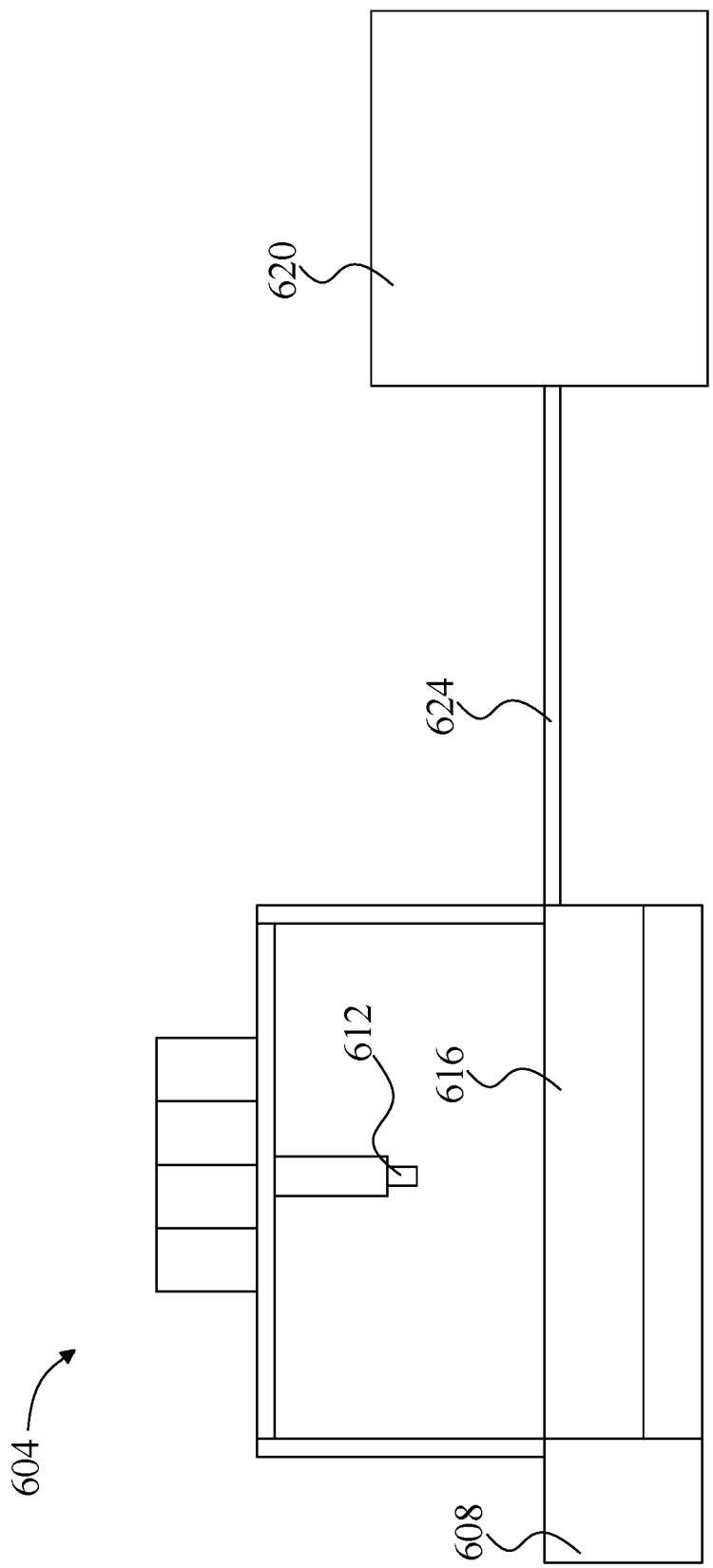
FIG. 6 is a schematic diagram of an exemplary embodiment of an automated manufacturing system.

Referring now to FIG. 6, a block diagram of an exemplary embodiment of an automated manufacturing system is illustrated. The automated manufacturing system includes an additive manufacturing device 604 and controller 608. Additive manufacturing device 604 may include at least an applicator 612. At least an applicator 612 may include any device used to deposit layers of food. For instance, applicator 604 may include a printer head for a 3D printer. Applicator 612 may include an extruding device for extruding fluid or paste material, a sprayer or other applicator for bonding material, an applicator for powering, a sintering device such as a laser, or other such material. Applicator 612 may draw upon one or more reservoirs of liquid, paste, and/or powdered materials, which may advance such materials to application using, without limitation, auger screws, pistons, gravity, and/or pressure.

Continuing to view FIG. 6, additive manufacturing device 604 may include a workpiece support 616. Workpiece support 616 may be a structure that supports a workpiece during the one or more manufacturing steps. Workpiece support 616 may include a base table. Base table may include a surface to which a workpiece or other components may be secured. Surface may be oriented horizontally, vertically, or in any other orientation. Surface may be substantially planar. Workpiece support 616 may include a substrate for initial deposition of material in an additive process.

Additive manufacturing device 604 may include a powered additive manufacturing device. As used herein, a powered additive manufacturing device is an additive manufacturing device 604 in which at least one component of the additive manufacturing device 604 includes at least a component powered by something other than human power. At least a component may be powered by any non-human source, including without limitation electric power generated or stored by any means, heat engines including steam, internal combustion, or diesel engines, wind power, waterpower, pneumatic power, or hydraulic power. Powered components may include any components of additive manufacturing device 604. Applicator 612 may be powered; for instance, applicator 612 may include an endmill mounted on a spindle rotated by a motor (not shown). Workpiece support 616 may be powered. Where additive manufacturing device 604 is a mechanical device, motion of components along linear or rotary constraints may be powered; for instance, motion of base table along one or more linear constraints such as linear slides may be driven by a motor or other source of power. Similarly, rotation of rotary table may be driven by a power source. Tool-changer, where present, may be driven by power. In some embodiments, all or substantially all of the components of additive manufacturing device 604 are powered by something other than human power; for instance, all components may be powered by electrical power.

Still referring to FIG. 6, Controller 608 may include a sequential control device that produces a sequence of commands without feedback from other components of automated manufacturing system. Controller 608 may include a feedback control device that produces commands triggered or modified by feedback from other components. Controller 608 may perform both sequential and feedback control. In some embodiments, controller 608 includes a mechanical device. In other embodiments, controller 608 includes an electronic device. Electronic device may include digital or analog electronic components, including without limitation one or more logic circuits, such one or more logic gates, programmable elements such as field-programmable arrays, multiplexors, one or more operational amplifiers, one or more diodes, one or more transistors, one or more comparators, and one or more integrators. Electronic device may include a processor. Electronic device may include a computing device 104. Computing device 104 may include any computing device 104 as described below in reference to FIG. 5. Computing device 104 may include a computing device 104 embedded in additive manufacturing device 604; as a non-limiting example, computing device 104 may include a microcontroller 608, which may be housed in a unit that combines the other components of additive manufacturing device 604. Controller 608 may include a manufacturer client of plurality of manufacturer clients; controller 608 may be communicatively coupled to a manufacturer client of plurality of manufacturer clients.

Controller 608 may include a component embedded in additive manufacturing device 604; as a non-limiting example, controller 608 may include a microcontroller 608, which may be housed in a unit that combines the other components of additive manufacturing device 604. Further continuing the example, microcontroller 608 may have program memory, which may enable microcontroller 608 to load a program that directs additive manufacturing device 604 to perform an automated manufacturing process. In other embodiments, controller 608 includes a computing device 104 that is separate from the rest of the components of additive manufacturing device 604; for instance, controller 608 may include a personal computer, laptop, or workstation connected to the remainder of additive manufacturing device 604 by a wired or wireless data connection. In some embodiments, controller 608 includes both a personal computing device 104 where a user may enter instructions to generate a program for turning workpiece into a finished product, and an embedded device that receives the program from the personal computing device 104 and executes the program. Persons skilled in the art will be aware of various ways that a controller 608, which may include one or more computing device, may be connected to or incorporated in an automated manufacturing system as described above.

Controller 608 may control components of automated manufacturing system; for instance, controller 608 may control elements including without limitation tool changer to switch endmills, spindle or gear systems operatively coupled to spindle to regulate spindle rotational speed, linear movement of applicator 612, base table, or both, and rotation or rotational position of rotary table. As an example, applicator 612 may be moved about using computerized numerical control (CNC) devices and/or motion controls that are automated and operate by precisely programmed commands that control movement of one or more parts of the equipment to affect the material removal. CNC machines, their operation, programming, and relation to computer aided manufacturing (CAM) tools and computer aided design (CAD) tools are well known and need not be described in detail herein for those skilled in the art to understand the scope of the present invention and how to practice it in any of its widely varying forms. Similarly, controller 608 may coordinate deposition and/or curing of material in additive manufacturing processes, where additive manufacturing device 604 is an additive manufacturing device 604. Persons skilled in the art, upon reading the entirety of this disclosure, will be aware of similar automated control systems usable for various forms manufacturing. Controller may be, be included in, include, and/or be in communication with computing device 104.

Still referring to FIG. 6, additive manufacturing device 604 may include an oven 620 or other heat source in which and/or with which a partially or wholly completed food product may be cooked, baked, heated, or the like; alternatively or additionally, a laser or other heat source at applicator may apply heat to food products in process of manufacture. One or more conveyors 624 may transfer food products between support structure and oven 620 or other components.

In operation, additive manufacturing device 604 may deposit layers of edible material, including without limitation powdered supplements and/or substrates, as programmed by computing device 104 and/or controller 608.

Computing device 104 may receive a plurality of ingredients, where receiving in this context refers to receiving data describing the plurality of ingredients. Plurality of ingredients may include one or more supplements in powdered form: applicator and/or other components of additive manufacturing device 604 may be controllable to administer and/or apply precise quantities of each powdered supplement, such that exactly an amount needed, as determined above, is applied and no more. Plurality of ingredients may include at least a substrate ingredient, where a "substrate ingredient" is an ingredient that acts as a binder and/or as a layer of material on which and/or into which powdered supplement material may be placed. Plurality of ingredients may include one or more flavor ingredients, where "flavor ingredients" are defined for the purposes of this disclosure as ingredients that are used to produce one or more flavors, for instance as specified by a user; one or more flavors ingredients may include spices, sweeteners, salt, acids such as citric acid, sources of bitterness, and/or sources of umami. In an embodiment, a user may request one or more flavors and/or flavor profiles, which may be programmed into computing device 104 and/or controller 608; in other words, computing device 104 may receive a user flavor preference and select ingredient combination as a function of the user flavor preference. For instance, and without limitation, computing device 104 and/or controller 608 may be programmed to produce one or more preconfigured recipes, such as a chocolate bar recipe having chocolate ingredients and/or flavors, a caramel bar recipe having caramel deposited thereon, or the like. User may alternatively or additionally enter an instruction specifying a desired texture; in other words, computing device 104 may receive a user texture preference and select the ingredient combination as a function of the user texture preference. For instance, user may request a chewy or soft texture, and computing device 104 and/or controller 608 may use a gelatinous material combined with flour or the like to create a soft or chewy texture, while a request for a crunchy texture may result in inclusion of crunchy substrate materials and/or baking and/or toasting the serving at one or more stages of deposition to produce a crunchy texture. Users may request both flavors and textures simultaneously, resulting, for instance, in a chewy chocolate-flavored bar, a crunchy cinnamon-flavored bar, or the like. Computing device 104 is configured to initiate manufacture of a nutritional supplement serving at the additive manufacturing device. Initiation of manufacture may include performance of a first step in the removal from or deposition of material to create part; first step may include a particular milling or cutting operation, such as the performance of a registration cut, a first deposition of material in a fused deposition modeling process, or the like. First step may include location of a workpiece at an additive manufacturing device; location may include placement in a precise position and/or registration within a coordinate system used by additive manufacturing device to guide particular manufacturing steps. First step may include generation of a control instruction initiating manufacturing steps: generation of a control instruction may include transmission of a signal to initiate manufacture and/or transmission of any machine control instruction sets generated as described above, including without limitation transmission of information for localized and machine-specific machine-control instruction generation. Transmission may be direct or indirect: for instance, transmission may involve transmission to a remote device that relays transmission to an additive manufacturing device or computing device 104 coupled thereto, or transmission to an auxiliary computing device 104 or computer memory for transport to the additive manufacturing device and/or computing device 104 coupled thereto. System may produce toolpaths for use by automated device:

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
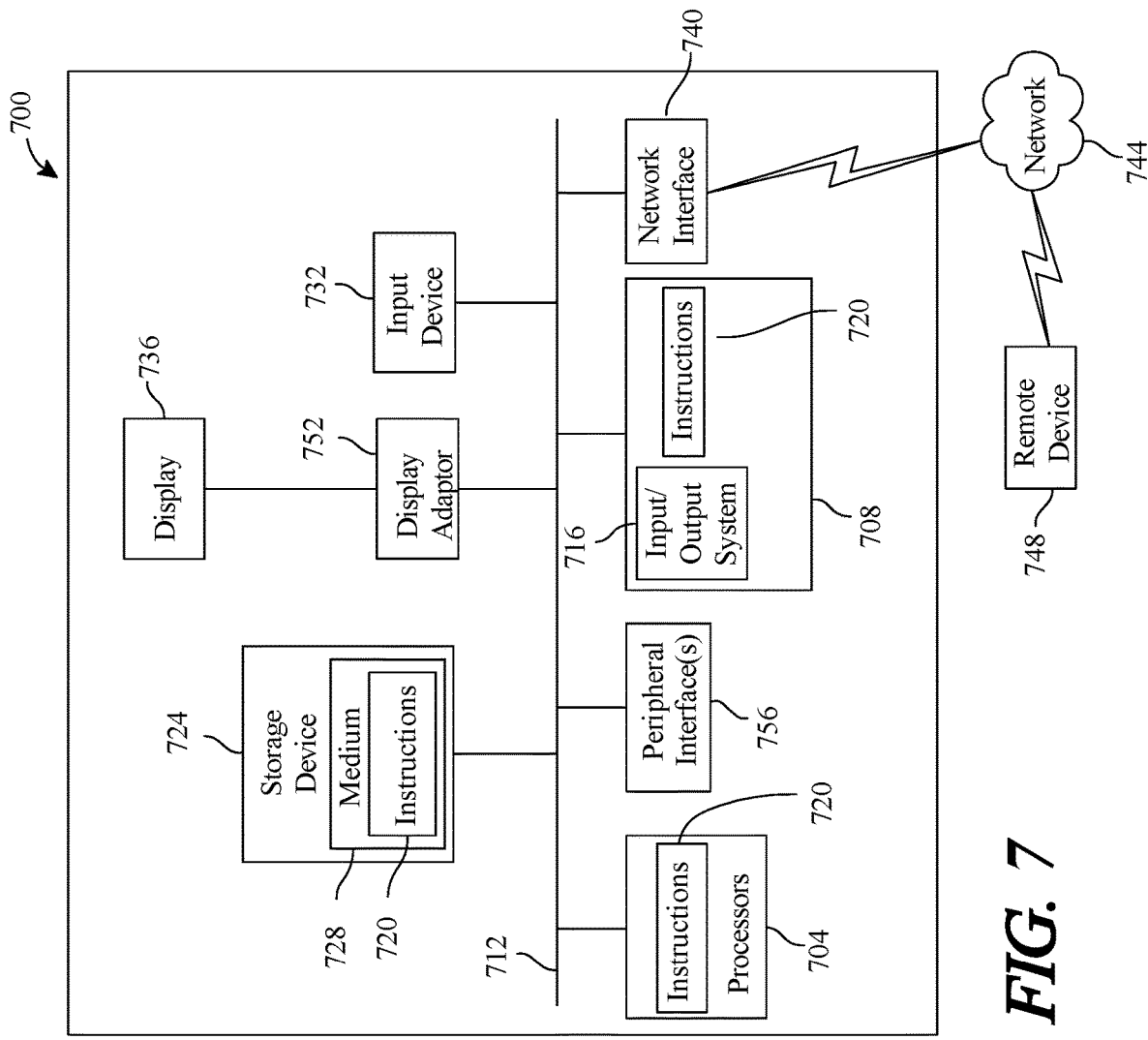
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures. Processor 704 may include any suitable processor, such as without limitation a processor incorporating logical circuitry for performing arithmetic and logical analysis processes, such as an arithmetic and logic unit (ALU), which may be regulated with a state machine and directed by analysis processual inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for initiating manufacturing of an edible combination, the system comprising a computing device, the computing device configured to:
   receive a first biological extraction related to a first biological system as a function of a monitoring device, wherein the monitoring device is configured to identify at least a biochemical concentration;
   identify at least a biochemical profile as a function of the first biological extraction received at a first time;
   generate a new profile, wherein generating the new profile comprises:
      obtaining a second biological extraction related to a second biological system, as a function of the monitoring device, received at a second time later than the first time, wherein the second biological system is different than the first biological system; and
      generating the new profile as a function of the second biological extraction;
   compare the biochemical profile and the new profile to identify at least a nutrient level offset from baseline nutrient levels of the biochemical profile; and
   determine an edible index using at least an edible directory to initiate manufacturing of an edible combination, selected as a function of the comparison between the biochemical profile and the new profile, using an automated manufacturing system, wherein the edible index comprises a classification representing each nutrient represented within the edible directory, wherein the automated manufacturing system comprises:
      a controller communicatively connected to the computing device,
      wherein the controller is configured to
         receive a user texture preference and a user flavor preference from the computing device, wherein the user texture preference comprises a crunchy texture, wherein the controller includes a sequential control device that produces a sequence of commands based on at least the user texture preference of the crunchy texture and the user flavor preference;

initiate the at least an applicator of the additive manufacturing device to deposit at least a portion of the at least a substrate ingredient and the at least a nutrient ingredient;

initiate a heat source of the additive manufacturing device to heat the deposited at least a portion to produce the crunchy texture; and an additive manufacturing device configured to execute additive manufacturing processes based on the sequence of commands produced by the controller, wherein the additive manufacturing device is connected to the controller by a wireless connection, the additive manufacturing device further configured to:

select at least a substrate ingredient and at least a nutrient ingredient as a function of the edible combination, the user texture preference of the crunchy texture, and the user flavor preference, wherein the at least a substrate ingredient comprises a crunchy substrate material; and add material in the form of a stack of incremental layers using at least an applicator connected to a computerized numerical control (CNC) device, wherein each layer represents a cross-section of an object to be formed, wherein each cross-section is sent and generated as a three-dimensional model of an object to be formed; and transfer the material from the at least an applicator to the heat source using a conveyor.

2. The system of claim 1, wherein first biological extraction includes at least a marker relating to a user biochemical status.

3. The system of claim 1, wherein the at least an edible directory comprises a database that relates to one or more markers associated with a user biochemical status.

4. The system of claim 1, wherein initiating the manufacturing of the edible combination further comprises initiating the manufacturing of the edible combination as a function of the edible index.

5. The system of claim 1, wherein the additive manufacturing device is further configured to transfer the at least a substrate ingredient from a reservoir to the applicator using an auger screw.

6. The system of claim 1, wherein the edible index further comprises a numerical value representing each nutrient represented within the edible directory.

7. A method for initiating manufacturing of an edible combination, the method comprising:

receiving, by a computing device, a first biological extraction related to a first biological system as a function of a monitoring device, wherein the monitoring device is configured to identify at least a biochemical concentration;

identifying, by the computing device, at least a biochemical profile as a function of a first biological extraction received at a first time;

generating, by the computing device, a new profile, wherein generating the new profile comprises:

obtaining a second biological extraction related to a second biological system, as a function of the monitoring device, received at a second time later than the first time, wherein the second biological system is different than the first biological system; and generating the new profile as a function of the second biological extraction;

comparing, by the computing device, the biochemical profile and the new profile to identify at least a nutrient level offset from baseline nutrient levels of the biochemical profile; and determining, by the computing device, an edible index using at least an edible directory to initiate manufacturing of an edible combination, selected based on the comparison between the biochemical profile and the new profile, using an automated manufacturing system, wherein the edible index comprises a classification representing each nutrient represented within the edible directory, wherein the automated manufacturing system comprises:

a controller communicatively connected to the computing device, wherein the controller is configured to receive a user texture preference and a user flavor preference from the computing device, wherein the user texture preference comprises a crunchy texture, wherein the controller includes a sequential control device that produces a sequence of commands based on at least the user texture preference of the crunchy texture and the user flavor preference;

initiate the at least an applicator of the additive manufacturing device to deposit at least a portion of the at least a substrate ingredient and the at least a nutrient ingredient; and initiate a heat source of the additive manufacturing device to heat the deposited at least a portion to produce the crunchy texture; and an additive manufacturing device configured to execute additive manufacturing processes based on the sequence of commands produced by the controller, wherein the additive manufacturing device is connected to the controller by a wireless connection, the additive manufacturing device further configured to:

select at least a substrate ingredient and at least a nutrient ingredient as a function of the edible combination, the user texture preference of the crunchy texture, and the user flavor preference, wherein the at least a substrate ingredient comprises a crunchy substrate material; and add material in the form of a stack of incremental layers using at least an applicator connected to a computerized numerical control (CNC) device, wherein each layer represents a cross-section of an object to be formed, wherein each cross-section is sent and generated as a three-dimensional model of an object to be formed; and transfer the material from the at least an applicator to the heat source using a conveyor.

8. The method of claim 7, wherein first biological extraction includes at least a marker relating to a user biochemical status.

9. The method of claim 7, wherein the at least an edible directory comprises a database that relates to one or more markers associated with a user biochemical status.

10. The method of claim 7, wherein initiating the manufacturing of the edible combination further comprises initiating the manufacturing of the edible combination as a function of the edible index.

11. The method of claim 7, wherein the additive manufacturing device is further configured to transfer the at least a substrate ingredient from a reservoir to the applicator using an auger screw.

12. The method of claim 7, wherein the edible index further comprises a numerical value representing each nutrient represented within the edible directory.

* * * * *